United States Patent [19]

Moxon et al.

[11] 4,344,315

[45] Aug. 17, 1982

[54] METHOD AND DEVICE FOR DISTINGUISHING MATERIAL BY THERMAL CONDUCTIVITY

[75] Inventors: Edwin C. Moxon, Boxboro; Wilson P. Menashi, Lexington, both of Mass.

[73] Assignee: Ceres Electronics Corporation, Waltham, Mass.

[21] Appl. No.: 213,560

[22] Filed: Dec. 5, 1980

Related U.S. Application Data

[63] Continuation of Ser. No. 974,649, Dec. 29, 1978, abandoned.

[51] Int. Cl.³ .................... G01N 25/18; G01N 27/18
[52] U.S. Cl. ................................................. 374/44
[58] Field of Search ......................... 73/15 R, 15 A

[56] References Cited

U.S. PATENT DOCUMENTS

| 2,951,360 | 9/1960 | Sampson | 73/15 |
| 3,611,786 | 10/1971 | Schorr | 73/15 |
| 3,668,927 | 6/1972 | Howell et al. | 73/154 |

FOREIGN PATENT DOCUMENTS

855658 12/1960 United Kingdom .................... 73/15

OTHER PUBLICATIONS

Sweat, "A Miniature Thermal Conductivity Probe for Foods".
Sandberg et al., "Heat Capacity and Thermal Conductivity from Pulsed Wire Probe", J. of Physics E., vol. 10, 1977, pp. 474-477.
Dittmar et al., "A Critical Examination of a Thermoconductivity Probe Used for Measurement of Local Blood Flow", International Conf. on Biomedical Transducers, 505-510, 1975.
Dittmar et al., "A Cyclically Controlled Device for a Thermoconductivity Probe Used in Measurements of Blood Flow", International Conf. on Biomed. Transducers, 353-359, 1975.
Ostinskaya et al., "A Experimental Device for Measurement of Thermal Conductivity of Diamond Monocrystals" in Inzhenerno-Fizicheskii Zhurnal, vol. 32 #4, pp. 620-624, 4/77.
Schulte, "A Pulsed Comparator for the Measurement of Thermal Conductivity" in Conf. Ther. Cond. 1970, pp. 589-598.
"Operation and Maintenence Manual for T-C100 Thermal Comparator", by Lafayette Instrument Co.

*Primary Examiner*—Herbert Goldstein
*Attorney, Agent, or Firm*—Hamilton, Brook, Smith and Reynolds

[57] ABSTRACT

Natural diamonds can be distinguished from simulated diamonds in seconds by merely touching a hand held probe to the gems. The tip of the probe includes a rounded gem contacting head of high thermal conductivity and low thermal mass. The head is preferably of gold-coated copper. It is supported on a high thermal resistivity neck extending from a large spring biased thermal mass. The head supports a thermistor heater element and a thermistor temperature sensing element within an annular space. Pulses of power are cyclically applied to the heater element to produce a predetermined amount of heat flow from the probe through the sample gem. The resulting change in temperature of the contacting head is determined by sensing the change in resistance of the sensing thermistor and weighting that change by the sensed thermistor resistance. The weighting function is carried out by a gain-controlled amplifier. The change-in-temperature signal controls a meter and LEDs which indicate whether the gem is natural or simulated.

30 Claims, 12 Drawing Figures

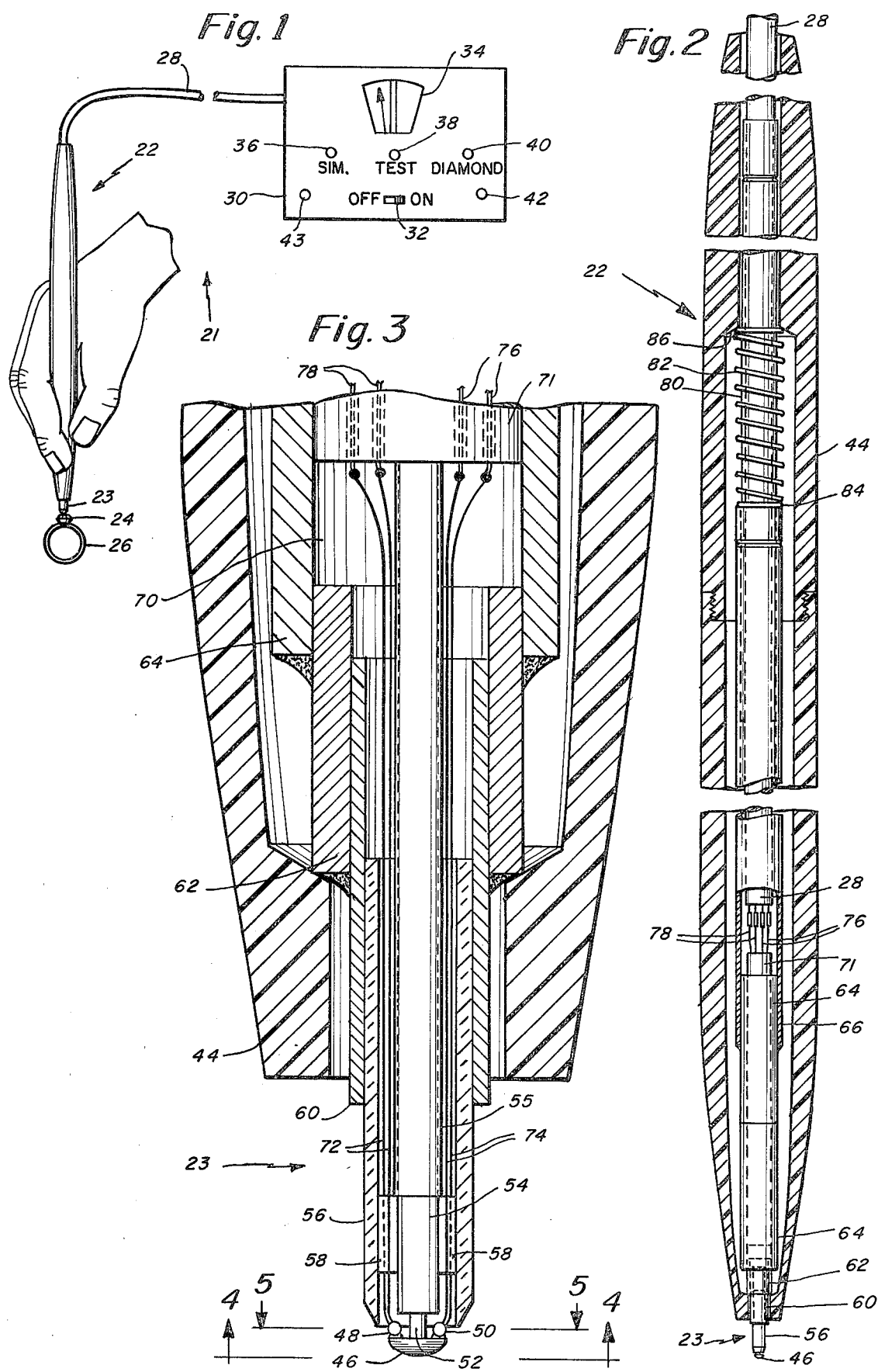

METHOD AND DEVICE FOR DISTINGUISHING MATERIAL BY THERMAL CONDUCTIVITY

This application is a continuation, of application Ser. No. 974,649, filed Dec. 29, 1978 now abandoned.

BACKGROUND OF THE INVENTION

This invention relates to methods and apparatus for distinguishing materials by their thermal conductivity and has particular application in distinguishing between natural and simulated gems by means of a hand held test probe.

Diamond-like gems produced from material other than carbon have found a significant commercial market. Some of these materials, such as cubic zirconia, have optical properties sufficiently similar to natural diamonds that experienced jewelers have difficulty in distinguishing the gem from natural diamond. The jeweler must remove the gem from its mounting to measure hardness and/or density or, with the gem in its mounting, make relatively complex X-ray tests that sometimes take several hours to perform. Because the hardness test requires scratching of the gem and the X-ray test requires equipment not readily available to jewelers, the density test is most commonly used. The density test does not lend itself to quick measurements with the gem left in its mounting.

In copending U.S. Patent Application Ser. No. 885,502, assigned to the assignee of the present invention, Leland Ashman has suggested that natural diamonds can be distinguished from simulated diamonds by means of a thermal conductivity test. This is because natural diamonds have a much higher thermal conductivity than do simulants. Where a simulant is so close in appearance to a natural diamond that it can not be readily distinguished by visual inspection, the thermal conductivity is distinctive.

The thermal conductivity of natural diamonds had previously been tested by Anthony Schorr using an apparatus disclosed in his U.S. Pat. No. 3,611,786. The device disclosed in that patent includes a small spherical diamond tip pressed against a suitably prepared diamond sample with a considerable force in the order of six million pounds per square inch. The probe is heated and the difference in temperature between the probe and a diamond supporting mass is used, along with the radius of a thermal contact area and the heat input rate, to determine the thermal conductivity of the diamond sample. Such a testing apparatus would not be suitable for use by a jeweler because of the size of the apparatus, the high pressure forces required, and the need for a measurement of temperature drop across the diamond sample. The latter requirement necessitates a first temperature sensor in the probe and a second temperature sensor in the diamond supporting mass.

The above disadvantages of the Schorr apparatus were overcome by Leland Ashman in the device disclosed in the above-mentioned application. In that application, method and apparatus are disclosed for quickly detecting the relative thermal conductivity of the material using a thermal probe. The probe contains a thermistor in circuit with a resistance bridge circuit. The thermistor is at the tip of the probe and is connected as a leg of the resistance bridge. While the probe tip is held firmly against the test material, such as an unknown gem, a controlled current pulse is fed to the thermistor to heat it, the probe tip and the gem. Immediately thereafter, while the probe tip is still against the gem, the change in resistance of the thermistor is indicated by the change in the balance of the bridge. This change in resistance is representative of change in temperature. It is compared with readings taken with the same or an associated probe on a reference material of known thermal conductivity to determine the relative thermal conductivity of the test gem. The reference material might be a natural diamond.

The method and apparatus taught in the copending Ashman application gives excellent results in distinguishing diamonds from zirconia and is a significant improvement over prior diamond testing devices. A gem can be distinguished within a few minutes after lightly touching a probe to a still-mounted gem. However, the device does require one or more steps of balancing the resistance bridge circuit. Also, the thermistor material is generally a poor thermal conductor compared to the other materials used in the probe tip. As a result, there may be a significant temperature drop within the thermistor when the reading is taken and that drop may mask the conductivity of the test gem. Such masking makes the device unreliable when used with some gems having greater thermal conductivity than zirconia. Furthermore, reliable results are dependent on the unknown gem and the reference material being at substantially identical thermal conditions. Any condition other than thermal conductivity which affects balance of the bridge circuit gives a false reading as to conductivity.

A principle object of the present invention is to provide a method and apparatus for testing diamond-like gems to determine whether the gems are natural or simulated.

A further object of the invention is to provide such a test apparatus which provides a reliable readout within seconds by merely touching a probe to a still-mounted gem.

The invention has further application to the testing of other materials.

SUMMARY

According to the invention in one of its aspects, a test probe includes a rounded sample contacting head of high thermal conductivity and a low thermal mass. A temperature sensing element is mounted to a back surface of the sample contacting head in thermal contact with the head. And a head supporting neck of moderate thermal resistivity extends from a relatively large thermal mass and supports the sample contacting head.

According to a further aspect of the invention, the sample contacting head is formed of material having a thermal conductivity of at least two watts per centimeter per degree Kelvin and a surface hardness within the range of 1.5 to 6 on the Moh's scale and preferably in the range of 2 to 3.

According to yet another aspect of the invention, the probe head supports separate heating and temperature sensing thermistors. An electrical circuit is connected to the temperature sensing thermistor to provide an indication of temperature change when the heat source thermistor is energized and de-energized.

According to the method of the present invention, an impulse of thermal power is applied to the sample contacting head and the resulting change in resistance of a temperature sensing resistor is sensed. The change in resistance is weighted by a sensed resistance to give an indication of change in temperature.

In accordance with a further aspect of the method of the present invention, the thermal pulses of power are applied cyclically to provide repetitive tests not affected by changes in conditions such as the temperature of the gem.

BRIEF DESCRIPTION OF THE DRAWINGS

The foregoing and other objects, features, and advantages of the invention will be apparent from the following more particular description of a preferred embodiment of the invention, as illustrated in the accompanying drawings in which like reference characters refer to the same parts throughout the different views. The drawings are not necessarily to scale, emphasis instead being placed upon illustrating the principles of the invention.

FIG. 1 is a pictorial illustration of a diamond testing device embodying the present invention;

FIG. 2 is a longitudinal sectional view of the test probe of FIG. 1;

FIG. 3 is a longitudinal sectional view of the tip of the probe of FIG. 2, greatly enlarged;

DESCRIPTION OF A PREFERRED EMBODIMENT

Figure 4:
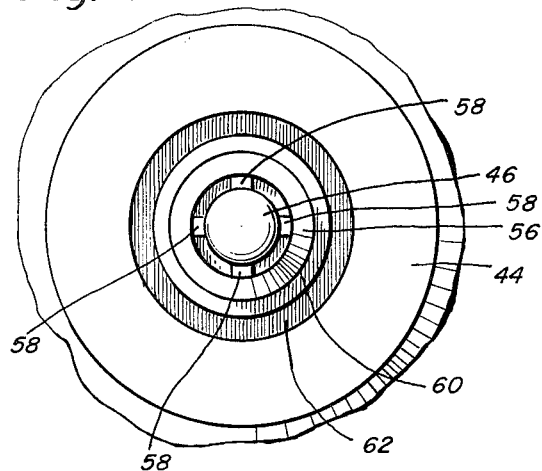
FIG. 4 is an end view of the probe of FIG. 3 taken along line 4—4.
Figure 5:
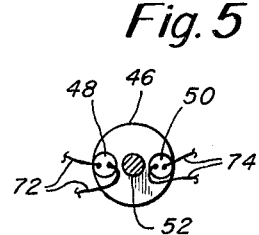
FIG. 5 is a cross-sectional view of the probe of FIG. 3 taken along line 5—5 and showing the thermistors mounted to the gem contacting head.

As shown in FIG. 1, a hand held probe 22 is placed with its tip 23 against a gem 54. The gem may be mounted in a ring 26 or the like and such mounting will not affect the testing.

A cable 28 connects the probe 22 to a meter box 30. When the switch 32 is turned on, and the tip 23 of the probe contacts the gem, the needle of the meter 34 will move to the right of center if the gem is a natural diamond but will remain to the left of center if the gem is other than a natural diamond. Display lights 36, 38 and 40 are also provided to give a parallel readout.

For calibrating the meter, and more particularly for testing its operation, a small mass of copper 42 and a small mass of sapphire 43 are provided on the face of the meter box 30. Copper has a thermal conductivity less than that of natural diamonds but greater than that of simulated diamonds. And sapphire has greater conductivity than the common simulants but less conductivity than copper. Thus, these materials provide convenient references for calibration.

When the meter is properly calibrated and otherwise functioning properly, the needle moves into the green diamond zone when the probe tip 23 contacts the copper mass 42. A diamond would move the needle further into the green zone. Similarly, when the sapphire is contacted, the needle moves into the red simulant zone. And other simulants move the needle further into the red zone. Because it is important that good thermal contact be made between the tip 23 and the gem 24, any accumulation of oil or other foreign matter on the tip can result in improper readings. A test with the copper and sapphire masses 42 and 43 assures that the diamond testing device is functioning properly.

A longitudinal sectional view of the probe 22 is shown in FIG. 2. The operative elements of the probe are housed in a plastic pen-like body 44. As shown in the enlarged view of the probe tip 23 in FIG. 3, the gem contacting surface is the rounded end surface of a copper head 46. The rounded end surface provides better thermal contact with a gem than would a pointed end. It is also preferred over a flat end because the latter would require normal incidence against a flat surface. The copper head is gold plated along its rounded surface to prevent development of oxides or other products of chemical reaction which might increase the thermal resistance of a thermal contact with the gem.

A heating thermistor 48 and a temperature sensing thermistor 50 are each mounted to the back side of the head 46 by high thermal conductivity epoxy. The epoxy also provides electrical insulation.

Although resistive heating elements other than thermistors are available, the thermistor is preferred because of its small size (about $1.3 \times 10^{-5}$ cubic centimeters) and its resultantly low thermal mass. Further, the heating element might be replaced with a heat pump such as a thermoelectric Peltier effect device. Such a device is able to inject and extract heat from the gem contacting heat 46. However, it is more fragile than the thermistor and has higher current consumption.

The gem contacting head 46 is mounted to a brass neck 52 by solder or the like. The neck 52 is an extension of a brass rod 54 machined to a reduced diameter. The reduced diameter of the neck 52 serves to increase the thermal resistance from the gem contacting head 46 to the brass thermal mass 54. It also provides an annular space between the head and the rod where the thermistors 48 and 50 are mounted. The thermistors are protected in the space by the gem contacting head.

The brass rod 54 is surrounded by close-fitting Teflon (a trademark for polytetrafluorethylene) tubing 55 which serves as an electrical insulator to prevent shorting of the fine thermistor wires 72 and 74. The rod 54 is also surrounded by a ceramic tube 56 which provides mechanical protection and electrical insulation. The end of the rod 54 adjacent the gem contacting head 46 is centered within the ceramic tube 56 by epoxy spacers 58. Four spacers are molded circumferentially around the rod 54.

The ceramic tube 56 is set in a brass tube 60. The tube is telescoped into increasing diameter tubes 62, 64 and 66 (FIG. 2) which are also of brass. The tubes 60, 62 and 64, having inner diameters greater than the diameter of the brass rod 54 define a space 70. That space 70 terminates at a ceramic, multibore rod 71. The ceramic rod 71 is glued within the brass tubes 64 and 65. The end of the brass rod 54 opposite to the gem contacting head 46 is secured in a bore in the ceramic rod 71.

Fine one mil wires 72 and 74 from the thermistors pass through the annular space between rod 54 and the ceramic tube 56 and into the space 70. There the fine wire is soldered to heavier wire which passes through the ceramic rod 71. At the other end of the rod 71 that heavier wire is spliced with wire in the multiconductor cable 28.

The brass tube 66 is crimped around the brass tube 80, and the tube 80 is in turn crimped to the cable 28. A spring 82 surrounds the tube 80 and is in compression between the shoulder 84 at the end of tube 66 and the plastic internal shoulder 86 of the pen housing 44. All of the internal components of the probe are slidable within the housing 44. Thus, if excessive pressure is applied by the user against a gem, the above-described components will retract against the spring 82. The likelihood of damage to the probe tip 23, delicate because of its small dimensions, is thereby reduced.

For purposes of assembly, the pen housing 44 is in two pieces having complementary threads. To strengthen the tip end of the housing, a ferrule may be used.

Figure 6:
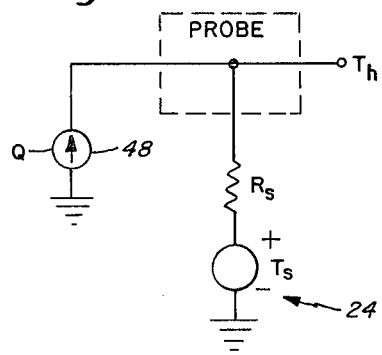
FIG. 6 is a schematic diagram of a thermal circuit illustrating the case of an ideal probe positioned against a gem.

It is convenient to illustrate the principle of operation of the probe by considering the essential features in a simplified model. FIG. 6 shows a schematic diagram of the thermal operation of a probe in an ideal case. In the ideal case connections are perfect; that is, there are no temperature differences within the probe tip, there are no spurious heat paths from the probe tip to the rest of the probe, and thermal masses are negligible. In other words, the probe tip is infinitely small and is held by a perfect thermal insulator and all heat generated at the probe flows into the gem and is conducted through its thermal resistance to ambient.

Electrical power is converted to thermal power in the thermistor heating element 48. With constant power input, the probe is subjected to a constant heat flow Q. This constant heat flow source 48 is analogous to an electrical constant current source. The heat flow is driven through the thermal resistance Rs of the sample gem. That thermal resistance is analogous to electrical resistance. The sample gem has an unheated temperature Ts which is usually ambient temperature. The gem at temperature Ts acts as a heat source analogous to an electrical voltage source. Ts is generally unknown and will vary with the environment. The temperature T of the gem contacting head 46, analogous to a voltage, is sensed by the temperature sensing thermistor.

Figure 7:
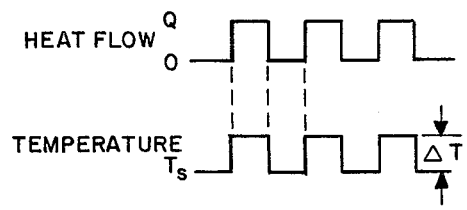
FIG. 7 is a timing chart of the heat flow from the heat flow source of the schematic of FIG. 6 and of the temperature of the probe.

In accordance with the device of the present invention, the heat flow Q is alternately applied by pulses of power as shown by the wave form of FIG. 7. The temperature of the probe rises and falls with the heat flow. The change in temperature of the probe, $\Delta T$, is equal to the temperature drop across the resistance Rs with constant heat flow Q. That temperature drop is equal to the product of the heat flow Q and the thermal resistance Rs. The change in temperature is not dependent on the temperature of the sample but is a change from that temperature.

Thus, with a known input of heat flow the thermal resistance of the gem from the probe tip can be determined. Thermal resistance is dependent on both thermal conductivity, which is the bulk property of interest, and geometries of the heat path. However, by use of an extremely small area of contact between the probe and gem, the effects of the gem geometry are virtually eliminated for gems of about 0.03 carat size or greater.

Figure 10:
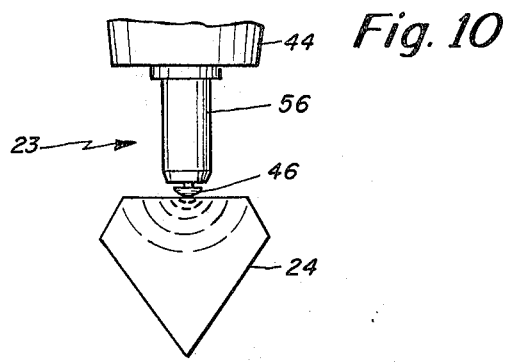
FIG. 10 illustrates the independence of conductivity measurements from gem geometry.

As illustrated in FIG. 10, the area through which heat flows from the probe tip 23 increases with the square of the distance from the tip. Thermal resistance is inversely related to that area; thus, the thermal resistance of the gem to the heat flow Q rapidly decreases with the distance from the probe tip. Beyond a short distance from the probe tip, the resistance of the gem is an insignificant part of the resistance Rs. Consequently, so long as the area of contact is very small relative to the size of the gem, the resistance Rs is determined only by that portion of the gem very close to the probe tip and is independent of any geometry of the gem. Differences in resistance of gems to the heat flow Q is dependent only on thermal conductivity, and the change in temperature $\Delta T$ can be used directly to determine that thermal conductivity.

Figure 8:
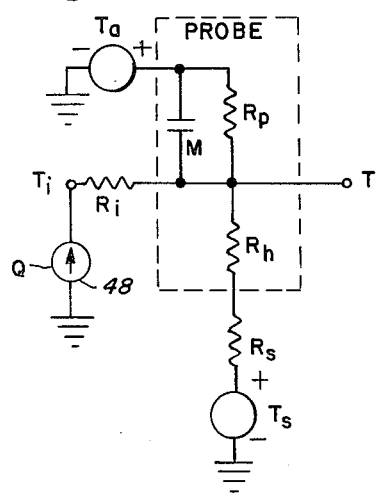
FIG. 8 is a more detailed schematic diagram of the probe thermal circuit including the thermal mass and thermal resistances of the probe.

The thermal circuit of FIG. 6 represents an ideal case, and for a more complete analysis additional factors must be considered. As shown in FIG. 8, the probe is not perfectly insulated. There is a thermal resistance Rp, less than infinity, from the probe to ambient, ambient being represented by a heat source of a temperature Ta. Gem contacting head 46 has a thermal resistance Rh, between the thermistors and the gem, and a thermal mass M.

Because the thermal resistance Rp is not infinite and the resistance Rh is not zero, temperature T is less sensitive than in the ideal case to changes in the thermal resistance Rs of the gem. However, the change in temperature $\Delta T$ still varies monotonically with changes in the gem resistance Rs. And so long as the resistance Rp is very large and the resistance Rh is small, the change in temperature due to heat flow from heater 48 is a measurable quantity.

Because sensitivity of the device deteriorates as the head resistance Rh becomes great with respect to the gem resistance Rs, the small head at the tip of the probe is of a material of high thermal conductivity. For the same reason, the distance between the thermistors and the contact area of the head is kept to a minimum.

A resistance Ri indicated in FIG. 8 is the resistance between the interior of the heating thermistor 48 and the probe structure. This schematic highlights the advantage of separate thermistors rather than the single thermistor used by Ashman. With the single thermistor the temperature Ri is sensed. And with the high internal resistance Ri of the heating thermistor between the contact area and the temperature sensing point, the resistance Rs is masked, thereby reducing sensitivity to the thermal conductivity of the gem.

Figure 9:
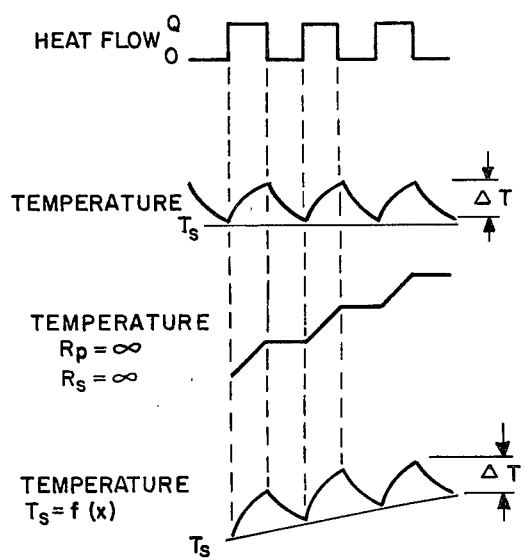
FIG. 9 is a timing chart of the heat flow from the thermal source, of the temperature at the temperature sensor of the probe, of the same temperature if the thermal resistance across the thermal mass of the probe were infinite, and of the same temperature if the gem temperature varies.

The effect of the thermal mass of the probe can be seen in the first temperature graph of FIG. 9. The temperature at the temperature sensing thermistor does not change instantaneously with changes in heat flow. Rather, the thermal mass of the head 46 and thermistors 48 and 50 results in a time constant in the response. Thus, the power pulse to the heater must be for a sufficient time to permit the temperature to approach equilibrium at each temperature level. In order to obtain a quick response, the thermal mass of the probe head must be held to a minimum. For that reason the gem contacting head is as small as feasible. In the present embodiment, it is 0.025 inches in diameter and 0.008 inches thick. The power pulses in this system are of one second duration. Thus the thermal mass of the head is such that the head time constant for temperature change is in the order of one second as shown in FIG. 9.

Given a thermal mass M of the head 46, the thermal resistance from the head 46 should not be infinite. If Rp were infinite and Rs were also infinite, as when no gem is contacted, the temperature would only increase as the pulses of power were integrated and stored in the thermal mass. This indicates that a finite value of Rp is actually desirable in order to discharge the heat collected in the thermal mass of the gem contacting head. For that reason, the head is mounted on a brass neck and not on a thermal insulator. Brass has only a moderate thermal conductivity and the reduced diameter of the neck further increases its resistance. Thus, the resistance Rp is sufficiently high not to unduly affect the sensitivity of the head temperature to changes in sample gem conductivity; yet, the resistance is sufficiently low to cool the probe head when it does not contact a sample.

It will also be noted that the reduced diameter brass neck extends from a large thermal mass. That mass is sufficiently large that its temperature does not fluctuate greatly with heat flow to it from the heating thermistor.

One further observation may be made with reference to the last temperature graph of FIG. 9. That chart indicates a change in gem temperature as a function of some variable. The temperature change may be with the ambient or it may be the result of heat flow thermistor 48 or from a person holding the gem. Changing gem temperature has only a negligible effect on the temperature change $\Delta T$ with each one second pulse of thermal power. As shown in the graph, the time constant of the small gem contacting head is much shorter than the time constant of the much larger gem.

It has been noted that so long as the contact area between the probe and gem is very small, thermal resistance of the gem relative to the probe is dependent only on thermal conductivity. To obtain that condition it is necessary that the gem contacting head not flatten to such an extent that the area of contact becomes too great. To prevent excessive flattening of the rounded surface of the gem contacting head, it is necessary that the head have a surface hardness of at least 1.5 on the Mohs scale of hardness; and it is desirable that the hardness be over 2 on that scale.

On the other hand, it is important that the contacting surface not be too hard. For example, if a diamond tip were used, the hard diamond would not flatten at all absent substantial force and the contact area would be near zero. The resulting resistance across the contact would be near infinite, and the probe would be insensitive to the thermal conductivity of the sample gem. Nor would a flat diamond tip be adequate. The probe is hand held and it would be exceptionally difficult to place the tip flat against a sample gem. Any offset of the probe from normal incidence with the sample gem would result in a point contact at the edge of the flat surface.

With the present device, the gem contacting surface is rounded and the head is sufficiently soft to permit it to flatten slightly. The result is a good thermal contact over a limited circular area. To assure sufficient contact, it is necessary that the gem contacting head have a surface hardness less than 6 on the Mohs scale. And to require a minimal amount of pressure on the head, the hardness should be less than 3.

Four materials having thermal conductivity of at least the required two watts per centimeter per degree Kelvin and a surface hardness within the range of 2 to 3 on the Mohs scale are copper, gold, silver and aluminum. Each of those materials is suitable for use in the sample contacting head 46 but the preferred material is copper. In the present device the copper head is plated with gold along its outer surface to prevent development of oxides or other products of chemical reaction.

It can be seen from the above analysis that, to determine the thermal conductivity of a test gem, the gem contacting head 46 must be raised from a first thermal equilibrium to a second thermal equilibrium by the input of thermal power in the form of constant heat flow. In this regard, the terms first and second are used only for convenience. The change in equilibrium could be from the second, during power input, to the first.

To provide an indication of the conductivity of the gem, it is necessary that the change in temperature $\Delta T$ be determined. In the preferred embodiment a thermistor is the miniature temperature sensing element. The resistance of a thermistor changes a known percentage, on the order of three or four percent and 3.4 percent in the present case, with each centigrade degree of temperature change. Over the temperature range of operation contemplated in this application, this percentage parameter of the thermistor is substantially constant.

Because the change in resistance is a percentage, change in resistance alone is not directly related to change in temperature. For example, where the resistance is 1,000 ohms a one degree change in temperature will result in about a 34 ohm change in resistance. However, where the resistance of the thermistor is 2,000 ohms a one degree change in temperature will result in a change in resistance of twice that amount, or 68 ohms. It can be seen that with increasing temperature, and thus decreasing resistance of the thermistor, a given change in temperature results in a lesser change in resistance.

In the above mentioned patent application by Leland Ashman, the varying relationship between resistance and change in temperature is accounted for by comparing the test reading to a reading against some known standard. Presumably the standard gem is at the same temperature as the sample. In some applications, this approach has been found to be inadequate.

The device of the present invention has been provided with a probe having a minute gem contact area. As discussed above, for gems of the sizes contemplated, this virtually eliminates effects of geometry on thermal resistance and thus eliminates the need for a standard gem of identical geometry. It has also been recognized by the above thermal analysis that, by changing the heat flow to the gem, one can use the change in temperature of the single sample gem as an indication of thermal conductivity. There is no need for any concurrent comparison of the resistance readings to similar readings on a standard gem. The final step in the method of the present invention is to electronically compensate for the nonlinearity of a thermistor temperature sensing device, thereby finally obviating the use of a reference gem.

As noted above, for small changes in temperature the thermistor resistance changes a given percentage per degree centigrade of temperature change. This can be set forth in mathematical terms as follows:

$$R_H = R_C - a\Delta T R_C \qquad (1)$$

Where $R_H$ is the thermistor resistance at equilibrium with heat flow through the gem, $R_C$ is the thermistor resistance at equilibrium when heat flow is not applied and α is the absolute value of the temperature coefficient of the temperature sensing thermistor 50. Solving for the unknown ΔT recognized to be indicative of thermal conductivity of the gem, the following equation is obtained:

$$-\alpha \Delta T = \frac{R_H - R_C}{R_C} \quad (2)$$

Equation two suggests that, although change in temperature ΔT is not directly proportional to the change in resistance of the thermistor, it is proportional to that change in resistance weighted by the thermistor resistance $R_C$. In the present case, the change in resistance is taken from the cold equilibrium state. However, it should be recognized that the measurement could be run in reverse, first measuring the hot resistance and then noting the change in resistance to the cold resistance. In that case, the change in temperature would be as follows:

$$-\alpha \Delta T = \frac{R_H - R_C}{R_H} \quad (3)$$

It should be understood that equation one and thus equations two and three only apply for small changes in temperature. The equation is a linear approximation to a nonlinear temperature/resistance response. For purposes of the present application to diamond testing, either of the approximations noted in equations two and three will suffice; but it is recognized that neither presents an exact solution.

For convenience, equation two can be rewritten as follows:

$$-\alpha \Delta T = \frac{R_H}{R_C} - 1 \quad (4)$$

From equation four it should be recognized that a circuit which has an output which satisfied equation four will provide an indication of the change in temperature ΔT. This is accomplished by the circuit shown in FIG. 11. The signals a through e indicated on the circuit are illustrated in FIG. 12.

A digital timing control 90 applies a heating control signal a through a constant power driver 92 to the heating thermistor 48. With each high signal a, the power driver 92 provides a constant-power pulse to the heating thermistor 48. The thermistor 48 converts the electrical pulse to a pulse of constant thermal power which, as noted above, forces a constant heat flow into the gem. The signal a is cycled at one cycle per second.

The heating thermistor 48 has a change in resistance with temperature. If a constant current were fed through the thermistor, the power, that is the product $I^2R$ or $E^2/R$, would vary with temperature. A known technique for delivering substantially constant power to a load whose resistance may vary within certain limits from a nominal value is to drive the load from a matched source. For a given load resistance it is well known that the first derivative of power with respect to resistance is zero where the source resistance and the load resistance are equal or matched. Since the derivative is zero under these conditions the expression for power is, to first order, such that small changes in the resistance of the heater thermistor produce no change in power input and therefore heat flow output.

The temperature sensing thermistor 50 is in series with a current source 94 driven by the one kilohertz output of an oscillator 96. The relatively high frequency oscillator signal is used in the detection circuitry to obtain the advantages of ac coupling in that circuit. For purposes of the analysis below, the current from the current source 94 through the thermistor 50 might be a dc current. Due to the current source input the voltage across the thermistor 50 is proportional to the resistance of the thermistor. That voltage is applied through a gain-controlled ac amplifier 98 to a scaled summing circuit 100 where it is summed with a signal from the oscillator 86. That output is applied through a differential amplifier 102. The output, signal c, from the differential amplifier is applied through a feedback circuit including a synchronous rectifier and hold circuit 104 to adjust the gain of the gain-controlled amplifier 98. As will be noted below, this feedback circuit is enabled during the cold portion of the heater drive cycle. During a short increment of the hot portion of the heater cycle, the signal c is applied through a synchronous rectifier and hold circuit 106 to the output meter 34. The same signal is also applied through comparitors 110, 112 and 114 to respective light emitting diodes 116, 118 and 120. Those light emitting diodes illuminate the green, yellow and red indicators on the meter box.

Figure 11:
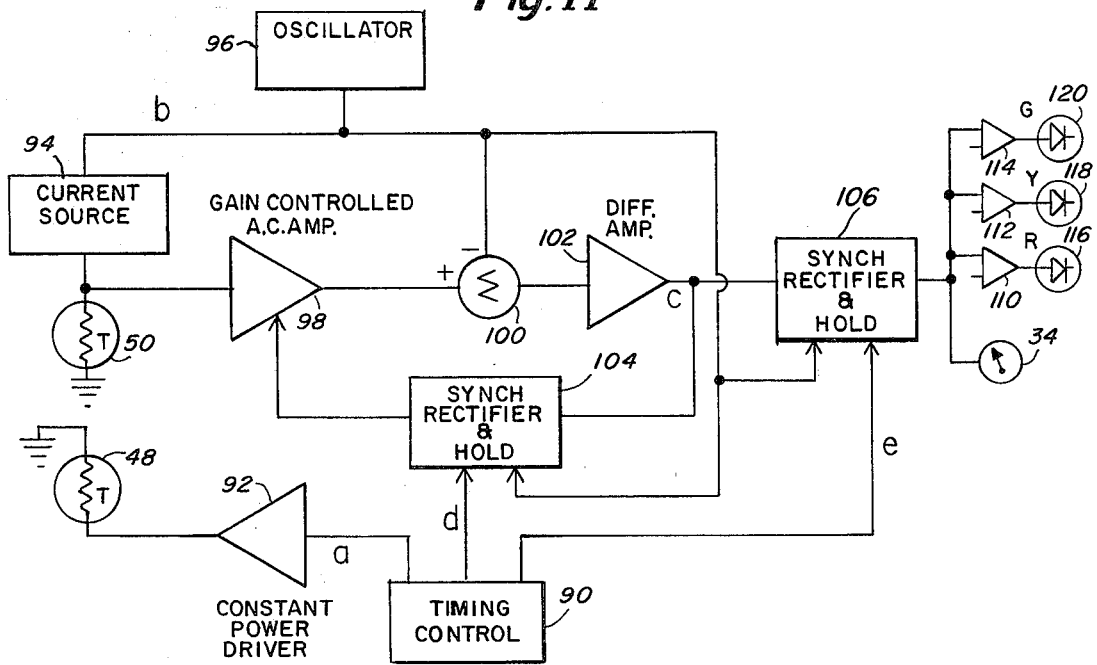
FIG. 11 is a block schematic diagram of an electrical circuit for implementing the present invention.
Figure 12:
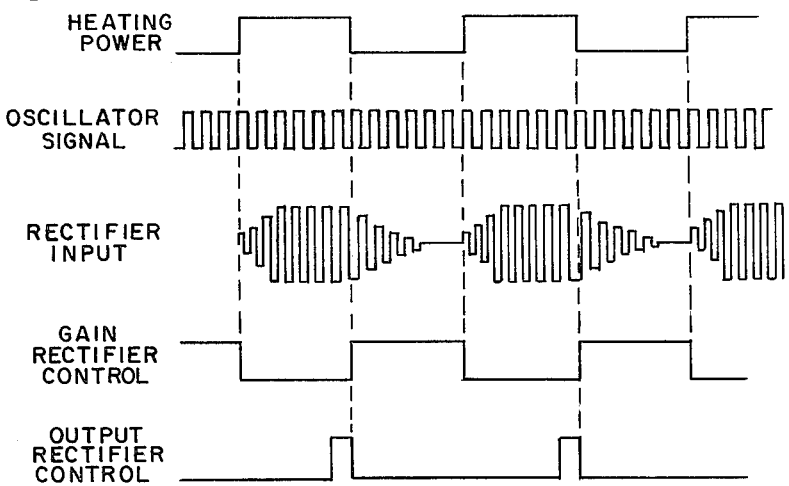
FIG. 12 is a timing chart of several signals in the circuit of FIG. 11.

Operation of the circuit of FIG. 11 is as follows. The oscillator signal b is applied continuously across the thermistor 50. During the cold portion of the heater cycle the synchronous rectifier and hold 104 is enabled by signal d. This circuit adjusts the gain of gain-controlled amplifier 98 to set the signal c to zero. The circuit is thereby normalized to the cold resistance $R_C$ of thermistor 50 and to the gem temperature. The synchronous rectifier 104 is then disabled and its output is held through the hot portion of the cycle to maintain a constant gain K in the amplifier 98.

The constant power driver 92 is then enabled and the voltage across the thermistor 50 begins to drop with increased temperature. That voltage is amplified by the normalized gain of amplifier 98 and applied through the summer 100 and differential amplifier 102. The synchronous rectifier 106 is not enabled until signal c has stabilized to the second equilibrium level. At the end of the hot portion of the heater cycle, the rectifier 106 is enabled by the pulse of signal e and the resulting dc signal is held on a capacitor for meter and indicator readout. The signal is held in circuit 106 until the next cycle. Thus, the readout is continuous and it is continuously updated, once every second.

The gain K of the amplifier is adjusted to provide an output c of zero during the cold portion of the cycle. This satisfies the following equation where a is a constant established by the summing circuit 100 and differential amplifier 102:

$$KV_C - a = 0 \quad (5)$$

From equation five it can be seen that the adjusted gain K subsequently held through the hot portion of the heater cycle, is as follows:

$$K = \frac{a}{V_C} \quad (6)$$

Thus, once the signal c has reached equilibrium during the hot portion of the cycles, the output signal at the input to the rectifier is:

$$\text{output} = \frac{a}{V_C} V_H - a \tag{7}$$

Equation seven can be simplified to:

$$\text{output} = \left(\frac{V_H}{V_C} - 1\right) a \tag{8}$$

From equation eight it is apparent that the output applied through the synchronous rectifier 106 to the meter and indicators is in the same form as equation four. Due to the current source 94, $V_H$ and $V_C$ are proportional to $R_H$ and $R_C$ respectively and the current factor cancels out. Thus, by proper calibration of the circuit, the meter will provide an output reading proportional to the change in temperature $\Delta T$.

As already noted, the meter is calibrated to give a diamond zone readout when the probe contacts a material having the thermal conductivity of copper. It is then further calibrated by means of other standards to establish the sweep of the meter needle for materials of various conductivities. For example, the minimum conductivity of a diamond causes the needle to move a bit more into the diamond zone and higher conductivities cause the needle to move even further into the diamond zone. Similarly, the maximum conductivity of a commercial simulant such as sapphire causes the needle to move slightly into the simulant zone and lesser conductivity simulants cause the needle to move even further to the left into the simulant zone.

Because jewelers make substantial financial investments based on the readout obtained from the diamond testing device, it is extremely important that the jeweler be aware when the device is not functioning properly. For that purpose, circuitry may be provided to turn the device off if the battery supply goes too low. Also, if the temperature of the thermistor 50 goes above or below the contemplated temperature range for which the device is designed, the device will automatically shut down. The final safeguard has already been mentioned. Copper and sapphire masses are provided on the face of the device for assuring that the meter needle moves to the proper zones when the masses are contacted.

While the invention has been particularly shown and described with reference to a preferred embodiment thereof, it will be understood by those skilled in the art that various changes in form and details may be made therein without departing from the spirit and scope of the invention as defined by the appended claims.

What is claimed is:

1. A thermal conductivity testing probe including means for subjecting a sample to heat flow relative to the probe, the probe comprising:
   a sample contacting head of high thermal conductivity of at least about two watts per centimeter per degree Kelvin and of low thermal mass, the thermal conductivity and thermal mass of the head being such that the head time constant for temperature change is in the order of one second, the sample contacting head having a rounded end surface;
   heat flow and temperature sensing means mounted to and in thermal contact with a back surface of the sample contacting head opposite to the rounded end surface; and
   a head supporting neck extending between the sample contacting head, from the back surface thereof, and a relatively large thermal mass, the thermal resistance of the head supporting neck being such that it allows for heat flow from the head to the relatively large thermal mass which is substantially greater than the heat flow from the head to the surrounding environment, but that heat flow to the large thermal mass being substantially less than that of a contacted diamond sample.

2. A thermal testing probe as claimed in claim 1 wherein the heat flow and temperature sensing means comprises separate heating and temperature sensing elements mounted to the back surface of the sample contacting head in thermal contact with that head but spaced from each other.

3. A thermal testing probe as claimed in claim 2 wherein the temperature sensing element and heating element are thermistors.

4. A thermal testing probe as claimed in claim 1 wherein the sample contacting head is formed of a material having surface within the range of 1.5 to 6 on Moh's scale of hardness.

5. A thermal testing probe as claimed in claim 4 wherein the surface hardness is within the range of 2 to 3 on Moh's scale of hardness.

6. A thermal testing probe as claimed in claim 4 wherein the sample contacting head comprising copper, silver, gold or aluminum.

7. A thermal testing probe as claimed in claim 4 wherein the sample contacting head is copper, plated with gold along the sample contacting surface.

8. A thermal testing probe as claimed in claim 1 wherein the sample contacting head is in the order of 0.025 inches in diameter.

9. A thermal testing probe as claimed in claim 1 wherein the sample contacting head is spring biased with respect to a probe.

10. A thermal conductivity testing device comprising:
    a probe having a sample contacting head;
    means for applying thermal power to the sample contacting head;
    a temperature sensing electrical resistor for sensing the temperature of the sample contacting head; and
    an electrical circuit for determining the thermal conductivity of the sample as a function of the resistance change in the resistor with a change in thermal power to the sample contacting head between two levels, wherein the electrical circuit includes an amplifier which receives a signal indicative of the electrical resistance of the temperature sensing resistor, the gain of the amplifier is dynamically controlled to provide a predetermined output when the thermal power to the sample contacting head is at a first level, and the output from the circuit is derived from the output of the amplifier at that controlled gain when the thermal power is at a second level.

11. A thermal conductivity testing device as claimed in claim 10 wherein the gain is controlled through a feedback circuit including a signal hold circuit and the hold circuit is controlled to permit dynamic control of the gain when the thermal power to the sample contacting head is at said first level and to hold that gain where the thermal power is at said second level.

12. A thermal conductivity testing device as claimed in claim 11 wherein the means for applying thermal power applies the power cyclically and the electrical circuit includes a output signal hold circuit which holds an output signal derived when the power is at said second level.

13. A thermal conductivity testing device as claimed in claim 10 wherein the means for applying thermal power applies that power cyclically at a rate in the order of one cycle per second.

14. A method of determining the thermal conductivity of a test material comprising the steps of:
holding a test probe in thermal contact with the test material until the test material approaches a first thermal equilibrium and sensing the resistance of a resistor in the test probe;
subjecting the test material to a predetermined level of heat flow to or from the test probe until the test material approaches a second thermal equilibrium and sensing the resistance of the resistor in the test probe; and
providing an indication of the thermal conductivity of the test material as a function of the difference in sensed resistances weighted by a sensed resistance by means of an amplifier which receives a signal indicative of the electrical resistance of the temperature sensing resistor, the gain of the amplifier being dynamically controlled to provide a predetermined output when the thermal power to the sample contacting head is at a first level, and the output from the circuit being derived from the output of the amplifier at that controlled gain when the thermal power is at a second level.

15. A method of determining the thermal conductivity of a test material as claimed in claim 14 wherein the amplifier gain is controlled through a feedback circuit including a signal hold circuit, the hold circuit being controlled to permit dynamic control of the gain when the thermal power to the sample contacting head is at said first level and to hold that gain when the thermal power is at said second level.

16. A method for determining the thermal conductivity of a test material as claimed in claim 14 or 15 wherein the test material is subjected to heat flow cyclically.

17. A method of distinguishing gems by determining the thermal conductivity of a gem comprising the steps of:
holding the test probe in thermal contact with the gem;
cyclically subjecting the gem to two levels of heat flow to or from the test probe;
measuring the difference in probe temperatures at the two levels of heat flow; and
providing a continuous indication of the difference in probe temperatures, that indication being updated with each cycle of heat flow to make the indication independent of changes in temperature of the gem which changes are slow relative to the cycle time.

18. A thermal conductivity testing device suitable for distinguishing a sample gem comprising:
a probe having a high thermal conductivity sample contacting head of thermal conductivity of at least about two watts per centimeter per degree Kelvin for making contact with a sample gem, the thermal conductivity and thermal mass of the head being such that the head time constant for temperature change is in the order of one second;
means for changing the heat flow to or from the sample contacting head cyclically between first and second predetermined levels, the cycle period being in the order of one second;
a relatively high resistance thermal path from the sample contacting head to the main body of the probe, the thermal resistance of that path being less than the resistance of the surrounding environment for preventing excessive heating of the head when it is not contacting the sample;
temperature sensing means for sensing the temperature of the sample contacting head; and
an electrical circuit responsive to the temperature sensing means for providing an indication of change in temperature of the sample contacting head, the circuit including means for compensating for the temperature of the contacted gem and means for updating the indication with each cycle of heat flow.

19. A thermal conductivity testing device as claimed in claim 18 wherein:
the means for changing the heat flow and the temperature sensing means are separate thermistors mounted to and in close thermal contact with a back surface of the sample contacting head opposite to a sample contacting surface and
a head supporting neck extends between the sample contacting head, from the back surface thereof, and a relatively large thermal mass, the thermal resistance of the head supporting neck being such that it allows for heat flow from the head to the relatively large thermal mass which is substantially greater than the heat flow from the head to the surrounding environment, that heat flow to the large thermal mass being substantially less than that to a contacted diamond sample.

20. A thermal conductivity testing device as claimed in claim 18 or 19 wherein the means for changing the heat flow is energized by substantially constant-power electrical pulses.

21. A thermal conductivity testing probe having a small thermal mass tip with heating and temperature sensing means at the end of a larger main body of the probe, the probe characterized in that:
the tip comprises a heat flow element, a separate temperature sensing element, and a high conductivity sample contacting head in close thermal contact with both the heat flow element and the temperature sensing element, the thermal conductivity of the sample contacting head being at least about two watts per centimeter per degree Kelvin;
the thermal path from the tip to the main body of the probe is of relatively high thermal resistance but of less resistance than that of the surrounding environment for preventing excessive heating of the the head; and
the thermal mass and thermal conductivity of the elements forming the tip are such that the head time constant of the tip for temperature changes is in the order of one second.

22. A thermal conductivity testing device as claimed in claim 21 wherein the heat flow element is energized cyclically by substantially constant power pulses.

23. A thermal conductivity testing device as claimed in claim 21 or 22 including an electrical circuit which provides an indication of temperature change as a function of the resistance change in the temperature sensing thermistor weighted by the sensed resistance of the thermistor.

24. A thermal conductivity testing device as claimed in claim 21 wherein
the sample contacting head has a rounded sample contacting surface;
the heat source thermistor and temperature sensing thermistor are mounted to a back surface of the sample contacting head, opposite to the sample contacting surface, in thermal contact therewith; and
the sample contacting head is mounted to a neck of relatively high thermal resistivity material extending from a relatively large thermal mass.

25. A thermal conductivity testing device as claimed in claim 24 wherein the sample contacting head is spring biased relative to a probe housing.

26. A thermal conductivity testing device as claimed in claim 21 wherein the sample contacting head is formed of a material having surface hardness within the range of 1.5 to 6 Mohs' scale of hardness.

27. A thermal conductivity testing device as claimed in claim 26 wherein the surface hardness is within the range of 2 to 3 on Mohs' scale of hardness.

28. A thermal conductivity testing device as claimed in claim 26 wherein the sample contacting head comprises copper, silver, gold or aluminum.

29. A thermal conductivity testing device as claimed in claim 26 wherein the sample contacting head is copper, plated with gold along the sample contacting surface.

30. A thermal conductivity testing device suitable for distinguishing a sample gem comprising:
a probe having a high thermal conductivity sample contacting head of thermal conductivity of at least about two watts per centimeter per degree Kelvin for making contact with a sample gem, the thermal conductivity and thermal mass of the head being such that the head time constant for temperature change is in the order of one second;
means for changing the heat flow to or from the sample contacting head cyclically between first and second predetermined levels, the cycle period being in the order of one second;
a relatively high resistance thermal path from the sample contacting head to the main body of the probe, the thermal resistance of that path being less than the resistance of the surrounding environment for preventing excessive heating of the head when it is not contacting the sample; and
temperature sensing means for sensing the temperature of the sample contacting head.

* * * * *